(12) United States Patent
Virkler et al.

(10) Patent No.: US 8,557,277 B2
(45) Date of Patent: Oct. 15, 2013

(54) MEDICAL PRODUCTS INCLUDING MODIFIED EXTRACELLULAR MATRIX MATERIALS

(75) Inventors: Joel A. Virkler, Farmington, MI (US); Lal Ninan, Santa Rosa, CA (US); Bhavin Shah, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 158 days.

(21) Appl. No.: 12/780,271

(22) Filed: May 14, 2010

(65) Prior Publication Data

US 2010/0221310 A1 Sep. 2, 2010

Related U.S. Application Data

(63) Continuation of application No. PCT/US2008/008614, filed on Dec. 10, 2008.

(60) Provisional application No. 61/012,569, filed on Dec. 10, 2007.

(51) Int. Cl.
*A61K 9/00* (2006.01)
*A61K 9/14* (2006.01)
*A61F 13/00* (2006.01)

(52) U.S. Cl.
USPC ............ 424/443; 424/400; 424/422; 424/484

(58) Field of Classification Search
USPC .................................. 424/400, 422, 443, 484
See application file for complete search history.

(56) References Cited

U.S. PATENT DOCUMENTS

| | | | |
|---|---|---|---|
| 5,460,962 A | 10/1995 | Kemp | |
| 2003/0167088 A1 | 9/2003 | Abraham et al. | |
| 2005/0059150 A1* | 3/2005 | Guarino et al. | 435/370 |
| 2005/0154534 A1* | 7/2005 | Haaland et al. | 702/19 |
| 2006/0251702 A1* | 11/2006 | Janis et al. | 424/426 |

* cited by examiner

*Primary Examiner* — Ruth Davis
(74) *Attorney, Agent, or Firm* — Woodard, Emhardt, Moriarty, McNett & Henry LLP

(57) ABSTRACT

Described, in certain aspects, are medical products comprised of uniquely prepared remodelable extracellular matrix (ECM) materials retaining at least a portion of their native bioactivity. Also described are methods for forming and using such products. In one embodiment, an inventive product comprises a layer of remodelable ECM material modified through contact with periodic acid or a salt thereof. In some forms, such a modified ECM material layer includes non-native Schiff's base crosslinks within and/or between certain components of the ECM material (e.g., between two collagen molecules, two non-collagen molecules, and/or a collagen molecule and a non-collagen molecule). Other inventive products are comprised of various gels, foams, pastes, and formed, coherent, porous bodies at least containing ECM materials that have been modified in accordance with the present invention.

23 Claims, 1 Drawing Sheet

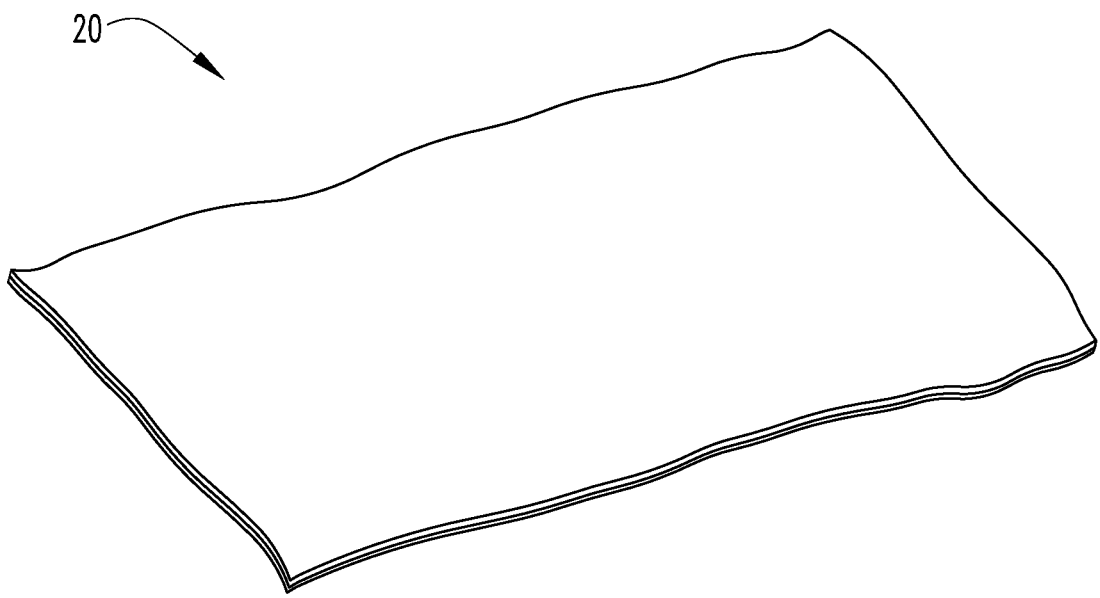

MEDICAL PRODUCTS INCLUDING MODIFIED EXTRACELLULAR MATRIX MATERIALS

REFERENCE TO RELATED APPLICATION

The present application is a continuation of PCT Patent Application Serial No. PCT/US2008/08614 filed Dec. 10, 2008, which was published in English under Article 21(2) and which claims the benefit of U.S. Provisional Patent Application Ser. No. 61/012,569 filed Dec. 10, 2007, expired, both entitled "MEDICAL PRODUCTS INCLUDING MODIFIED EXTRACELLULAR MATRIX MATERIALS", and both of which are hereby incorporated by reference in their entirety.

BACKGROUND

The present invention relates generally to medical devices and in particular aspects to medical products comprised of extracellular matrix materials.

As further background, collagen-containing materials have found wide use in the medical arts, particularly in applications involving tissue replacement, augmentation, and/or repair. Suitable collagenous materials can be provided by collagenous extracellular matrix (ECM) materials. Such ECM materials can be provided, for example, by materials isolated from a suitable tissue source from a warm-blooded vertebrate, e.g., from the submucosal tissue of a mammal. Such isolated submucosal tissue, for example, small intestinal submucosa (SIS), can be processed so as to have bioremodelable properties and promote cellular invasion and ingrowth. Illustratively, sheet-form SIS materials have been used as surgical grafts to provide tissue support in patients, e.g., in hernia repair operations. In some forms, the sheet-form SIS material includes a multilayered configuration to provide strength, reinforcement, and/or other enhancements to the graft.

It is also well known in the medical arts to treat or otherwise modify isolated collagenous materials. For example, such materials can be crosslinked, i.e., covalent crosslinks can be caused or allowed to form within the material (e.g., within and/or between certain components of the material) and/or between the material and another substance or material. Crosslinking can be used to enhance certain mechanical, chemical, biological, and/or other properties of a collagenous ECM material, for example, to increase the strength of the material and/or to decrease the biodegradation rate of the material. Several crosslinking techniques are known in the art including but not limited to photo-crosslinking, chemical crosslinking, and protein crosslinking induced by dehydration or other means.

Commonly used chemical crosslinkers include, for example, aldehydes such as glutaraldehydes, diimides such as carbodiimides, e.g., 1-ethyl-3-(3-dimethylaminopropyl) carbodiimide hydrochloride, acyl-azide, sulfo-N-hydroxysuccinamide, and polyepoxide compounds, including for example polyglycidyl ethers such as ethyleneglycol diglycidyl ether. While these and other crosslinking agents may be useful to crosslink collagenous materials, they can cause undesirable consequences as well. For example, exposure to such materials can destroy the remodelable properties of a remodelable collagenous ECM material. Also, crosslinking a collagenous ECM material with glutaraldehyde can lead to the formation of very high molecular weight glutaraldehyde polymers which are difficult to eliminate from the material, and therefore, may be subsequently released into the patient's body after implantation.

There remain needs for improved and/or alternative medical products that are comprised of ECM materials, as well as methods for manufacturing and using these products. The present invention is addressed to those needs.

SUMMARY

In one aspect of the invention, uniquely prepared ECM materials retaining at least a portion of their native bioactivity are provided. In particular embodiments, the invention provides medical graft materials comprising: (i) a layer of isolated remodelable ECM material that has been modified through contact with periodic acid or a salt thereof; and (ii) at least one bioactive agent retained in the modified ECM material layer, the bioactive agent being selected from the group consisting of a proteoglycan, a growth factor, a glycoprotein, and a glycosaminoglycan. Such an isolated remodelable ECM material layer may include a remodelable, angiogenic ECM material, for example, a submucosa material such as but not limited to porcine small intestinal submucosa (SIS). In some forms, an ECM material layer is modified to include non-native Schiff's base crosslinks in the ECM material, for example, within and/or between certain components of the ECM material (e.g., between two collagen molecules, two non-collagen molecules, and/or a collagen molecule and a non-collagen molecule of the ECM material). These and other inventive medical graft materials can be single layer devices, or alternatively, can be formed with two or more individual ECM material layers bonded or otherwise attached to one another.

In one aspect, the present invention provides a method of forming a medical graft material. In one step of the method, a first layer of isolated remodelable extracellular matrix material is provided. In another step, the first extracellular matrix material layer is contacted with periodic acid or a salt thereof for a period of time and under conditions effective to modify the first extracellular matrix material layer yet preserve at least one bioactive agent in the extracellular matrix material. The bioactive agent is selected from the group consisting of a proteoglycan, a growth factor, a glycoprotein, and a glycosaminoglycan.

In another embodiment, the invention provides a method of forming a medical graft material. As part of this method, a first layer of isolated remodelable extracellular matrix material and a second layer of isolated remodelable extracellular matrix material are provided. In another step, the first extracellular matrix material layer is positioned in contact with the second extracellular matrix material layer in the presence of periodic acid or a salt thereof and for a period of time and under conditions effective to bond the first extracellular matrix material layer to the second extracellular matrix material layer yet preserve at least one bioactive agent in each of the first extracellular matrix material layer and the second extracellular matrix material layer. The bioactive agent is selected from the group consisting of a proteoglycan, a growth factor, a glycoprotein, and a glycosaminoglycan.

In yet another embodiment, the present invention provides a medical product including a formed coherent porous body comprised of a particulate remodelable ECM material that has been contacted with periodic acid or a salt thereof for a period of time and under conditions effective to increase the coherency of the body yet preserve the activity of one or more growth factors retained in the ECM material. The one or more growth factors are selected from the group consisting of basic fibroblast growth factor, transforming growth factor beta, epidermal growth factor, and platelet derived growth factor. This medical product may, in certain embodiments, be provided in a substantially dried state.

The present invention also provides, in one aspect, a method of forming a coherent porous medical product. In one step of this method, a conformable mass comprising particulate remodelable ECM material is provided. In another step, the ECM material is contacted with periodic acid or a salt thereof for a period of time and under conditions effective to increase the coherency of the conformable mass yet preserve the activity of one or more growth factors retained in the ECM material. The one or more growth factors are selected from the group consisting of basic fibroblast growth factor, transforming growth factor beta, epidermal growth factor, and platelet derived growth factor. Such a conformable mass can, in some forms, comprise a flowable ECM material that is at least partially solubilized or otherwise denatured or disassembled relative to its native collagenous structure. Illustratively, a suitable conformable ECM material may comprise an ECM material paste, a fluidized ECM material, and/or gelatinous ECM material.

In another aspect, the present invention provides a medical product that is comprised of a dried porous body. This body comprises a network of reassembled collagenous extracellular matrix material, wherein the reassembled extracellular matrix material has been modified through contact with periodic acid or a salt thereof yet retains at least one bioactive agent selected from the group consisting of a proteoglycan, a growth factor, a glycoprotein, and a glycosaminoglycan.

The present invention also provides, in another embodiment, a medical graft material that includes a layer of isolated remodelable extracellular matrix material that has been modified to include Schiff's base crosslinks that were not present in the extracellular matrix material prior to modification. In this graft material, at least one bioactive agent is retained in the modified extracellular matrix material layer. The bioactive agent is selected from the group consisting of a proteoglycan, a growth factor, a glycoprotein, and a glycosaminoglycan.

Other objects, embodiments, forms, features, advantages, aspects, and benefits of the present invention shall become apparent from the detailed description and drawings included herein.

BRIEF DESCRIPTION OF THE DRAWINGS

FIG. 1 is a perspective view of a medical graft material according to one embodiment of the invention.

DETAILED DESCRIPTION

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, the present invention provides, in certain aspects, medical products comprised of uniquely prepared remodelable ECM materials retaining at least a portion of their native bioactivity. These products may be in the form of generally intact sheet or sheet-like products or other shaped products, or alternatively, may be provided in the form of gels, foams, pastes, and other similar products containing ECM materials prepared in accordance with the present invention. In one embodiment, the invention provides a medical graft material comprising: (i) a layer of isolated remodelable ECM material that has been modified through contact with periodic acid or a salt thereof; and (ii) at least one bioactive agent retained in the modified ECM material layer, the bioactive agent being selected from the group consisting of a proteoglycan, a growth factor, a glycoprotein, and a glycosaminoglycan. This modified ECM material layer can be a remodelable, angiogenic ECM material layer, for example, a submucosa material layer such as but not limited to porcine small intestinal submucosa (SIS) material layer. In some forms, modified yet bioactive ECM materials of the invention include non-native Schiff's base crosslinks in the ECM material, for example, within and/or between certain components of the ECM material (e.g., between two collagen molecules, two non-collagen molecules, and/or a collagen molecule and a non-collagen molecule of the ECM material). The invention also provides methods of forming and utilizing such medical graft materials, as well as medical products that include such materials enclosed within sterile packaging.

Suitable graft materials for use in the present invention are generally biocompatible, and in advantageous embodiments, are comprised of a remodelable material. Particular advantage can be provided by graft materials that comprise a remodelable collagenous material. Such remodelable collagenous materials, whether reconstituted or naturally-derived, can be provided, for example, by collagenous materials isolated from a warm-blooded vertebrate, and especially a mammal. Such isolated collagenous materials can be processed so as to have remodelable properties and promote cellular invasion and ingrowth. In this context, inventive graft products that include remodelable, angiogenic materials can actively promote patient tissue growth within sites in which these products are implanted.

Suitable remodelable materials can be provided by collagenous ECM materials possessing biotropic properties. For example, suitable collagenous materials include ECM materials such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

Submucosa tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

A suitable ECM starting material preferably comprises one or more bioactive substances native to the source of the ECM material. Illustratively, such bioactive substances can be comprised of amino acids having polar groups that are capable of interacting with other molecules. In certain preferred aspects, an ECM starting material retains one or more native bioactive agents such as but not limited to proteins, glycoproteins, proteoglycans, and glycosaminoglycans. For example, ECM materials may retain heparin, heparin sulfate, hyaluronic acid, fibronectin, cytokines, and the like. As well, an ECM starting material may retain one or more growth factors such as but not limited to basic fibroblast growth factor (FGF-2), transforming growth factor beta (TGF-beta), epidermal growth factor (EGF), platelet derived growth factor (PDGF), and/or cartilage derived growth factor (CDGF). Thus, generally speaking, a submucosa or other ECM starting material may retain one or more bioactive components that induce, directly or indirectly, a cellular response such as a change in cell morphology, proliferation, growth, or protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods, may be incorporated into an ECM material before, during, and/or after any processing step of the invention. These non-native bioactive components may be naturally-derived or recombinantly produced proteins that correspond to those natively occurring in an ECM tissue, but perhaps of a different species (e.g., human proteins applied to collagenous ECMs from other animals, such as pigs). Suitable non-native bioactive components may include one or more drug substances. Illustrative drug substances that may be added to an ECM material include, for example, anti-clotting agents (e.g., heparin), antibiotics, anti-inflammatory agents, thrombus-promoting substances such as blood clotting factors, e.g., thrombin, fibrinogen, and the like, and anti-proliferative agents (e.g., taxol derivatives such as paclitaxel). Such non-native bioactive components can be incorporated into and/or onto an ECM material in any suitable manner, for example, by surface treatment (e.g., spraying or brushing) and/or impregnation (e.g., soaking). Also, these substances may be applied to the ECM material in a pre-manufacturing step, immediately prior to the procedure (e.g., by soaking the material in a solution containing a suitable antibiotic such as cefazolin), or during or after engraftment of the material in the patient.

Inventive graft materials can include xenograft components (i.e., cross species material, such as tissue material from a non-human donor to a human recipient), allograft components (i.e., interspecies material, with tissue material from a donor of the same species as the recipient), and/or autograft components (i.e., where the donor and the recipient are the same individual). For example, in certain aspects of the invention, a graft product includes ECM tissue material, wherein the ECM material is xenogenic relative to the patient receiving the graft, and any added exogenous substances are from the same species (e.g. autologous or allogenic) as the patient receiving the graft. Illustratively, human patients may be treated with xenogenic ECM material (e.g. porcine-, bovine- or ovine-derived material) that has been combined with exogenous human material(s) as described herein, those exogenous materials being naturally derived and/or recombinantly produced.

Turning now to a discussion of particular inventive graft products and methods of preparing the same, it should be noted that suitable ECM starting materials come in a variety of forms. In certain aspects, an ECM starting material includes an isolated ECM material layer comprised of a network of collagen fibers retaining substantially its native structure, and in this regard, such an isolated material layer can undergo further processing in accordance with the present invention to enhance or otherwise modify one or more physical, chemical, biological, and/or other characteristics of the layer, for example, to form a single-layer modified ECM material product or to provide a component for a multi-layer construct. In other aspects as discussed more thoroughly below, a suitable ECM starting material includes a flowable or otherwise conformable collagenous ECM material that is at least partially solubilized or otherwise denatured or disassembled relative to its native network of collagen fibers and other ECM components. These and other suitable ECM starting materials can be further processed in accordance with the invention to selectively enhance or otherwise modify one or more physical, chemical, biological and/or other properties of the material such as but not limited to its mechanical integrity, density, anti-immunogenicity, and/or biostability. In this regard, components of an ECM material can be modified (e.g., crosslinked) without having to use cytotoxic coupling agents such as glutaraldehyde.

In particular embodiments, a modification is effective to generate a desired quantity of reactive aldehyde groups on components of an ECM starting material (whether these components are part of a collagen molecule or other molecule or substance native to the source of the ECM starting material), while at the same time preserving the activity of one or more bioactive substances retained in the ECM starting material. The production of such reactive aldehyde groups (e.g., aldehyde moieties, dialdehyde residues, etc.) can be accomplished in any suitable manner including but not limited to oxidizing carbohydrate moieties on components of the ECM material, for example, through contact with periodic acid or one or more salts thereof, such as sodium periodate, potassium periodate, and other alkali metal periodates. In some forms, a suitable ECM starting material also includes molecules not native to the source of the ECM material(s) present, and these molecules can be selectively modified to produce reactive aldehyde groups thereon. As one illustrative embodiment, an ECM starting material that is derived from a particular source (e.g., porcine tissue) may incorporate components that are derived from a different source, and these components (e.g., collagen and/or non-collagen components) may be modified as described herein.

Alternatively, ECM materials can be oxidized in a desirable fashion through contact with one or more other suitable oxidizing agents including but are not limited to hydrogen peroxide or other peroxides, diisocyanates, halogens, n-bromosuccinimide or other halogenated compounds, permanganates, ozone, chromic acid, sulfuryl chloride, sulfoxides, and selenoxides. Additionally, oxidation of an ECM material can be accomplished by heating the ECM material and/or irradiating the ECM material in a controlled manner (e.g., with alpha, beta, ultraviolet, electron beam, gamma rays) in the presence of oxygen (e.g., ambient oxygen, room air, gaseous oxygen). In some embodiments, these and other suitable oxidative processes are also used as bacterial activation processes. Nonetheless, because certain processing (e.g., oxidizing) steps can destroy the remodelable properties of a remodelable material, where preservation of remodelable properties is desired, any processing step can be performed to an extent or in a fashion that allows the material to retain at least a portion of its remodelable properties.

In some forms of the invention, an aldehyde group formed on a first component of an ECM starting material can be caused or allowed to react to crosslink that ECM component to itself or another component of the ECM starting material (e.g., to crosslink two collagen molecules, two non-collagen molecules, or a collagen molecule with a non-collagen molecule) through an imine bond (commonly referred to as a Schiff's base link) formed between the aldehyde of the first ECM component and an amine (lysine amino acid residue) on the same component or on another ECM component. Illustratively, such an amine can be provided by arginine, asparagine, glutamine or lysine. In one method, an ECM starting material is treated with periodic acid or a salt thereof for a period of time and under conditions effective to form intramolecular and/or intermolecular non-native Schiff's base crosslinks within the ECM starting material and/or between the ECM starting material and another amine-containing material or object (or at least promote and/or facilitate subsequent crosslinking within the ECM starting material and/or between the ECM starting material and another amine-containing material or object), while at the same time, preserving the activity of one or more bioactive substances retained in the ECM material.

When formed, amine linkages, and thus the crosslinked ECM material, may subsequently be stabilized by reduction with a mild reducing agent such as but not limited to a borohydride, like sodium borohydride ($NaBH_4$) or sodium cyanoborohydride ($NaBH_3CN$). The residual aldehyde groups may be consumed with ethanolamine or other amine-containing species to further modify the cross-linked ECM material. Such a reduction step can be used to help avoid an unacceptable inflammatory response when the modified ECM material is introduced to the patient's body.

In certain embodiments, an ECM starting material comprising a layer of isolated collagenous ECM material is suitably treated in accordance with the invention to produce reactive aldehyde groups on certain components of the ECM material layer, while at the same time, preserving at least a portion (and in some cases, a substantial portion) of the material's bioactivity. Thereafter, non-native Schiff's base crosslinks can be caused or allowed to form between and/or within components of the ECM material. Such non-native crosslinking can be used to enhance certain mechanical, biological, chemical, and/or other characteristics of the ECM sheet material.

In certain aspects, sheet-form ECM materials modified in accordance with the present invention are then subjected to additional processing. Illustratively, intermediate and end products of the invention may be subjected to one or more drying steps. For example, in some embodiments, a fully or partially hydrated "intermediate" graft material is subjected to drying conditions to prepare it for further processing. For example, a periodate-treated ECM sheet material can be dried and then ground (e.g., cryoground) to form a modified ECM particulate product. Such particulate products find wide application in the field of medicine, particular in applications involving tissue replacement, augmentation, and/or repair. In some forms, a modified particulate product is manufactured to possess certain enhanced characteristics such as but not limited to increased resistance to biodegradation upon implantation in a patient. Also, these particles can be incorporated into a suitable carrier, e.g., an ECM or non-ECM hyrdogel. In other embodiments, a fully or partially hydrated graft material "end product" is subjected to drying conditions to prepare it for use (and potentially also for transport and/or storage).

Turning now to a discussion of drying techniques that can be useful in certain embodiments of the invention, a lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described above.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

It is advantageous in some aspects of the invention to perform drying and other operations under relatively mild temperature exposure conditions that minimize deleterious effects upon the modified ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In other embodiments, a modification process of the invention may comprise coupling or otherwise bonding an ECM material to one or more other objects and/or materials. Illustratively, an inventive modification process may be used to incorporate (or at least promote and/or facilitate the incorporation of) one or more exogenous bioactive substances into and/or onto an ECM material. For example, an imine bond can be caused or allowed to form between an aldehyde moiety formed on a component of an ECM material and an amine group of a suitable bioactive substance, or vice versa. In certain preferred aspects, processing with sodium periodate leads to the coupling of a therapeutic substances (e.g., a drug) to an ECM material. Such a drug-carrying material can then be delivered to a treatment site, where it can dispense or otherwise release the drug. Also, aldehyde moieties formed on components of an ECM material in accordance with the invention can be used in whole or in part to covalently bond the ECM material to a suitable amine-containing surface, for example, to form an ECM coating layer on the surface. Such ECM coating layers find use in a wide variety of medical applications such as but not limited to in cell-seeding a surface and/or providing a coated medical device (e.g., a coated implantable graft, stent, embolization device, etc.).

In some modes of operation, aldehyde moieties formed on a surface of an isolated, sheet-form ECM material can be used to crosslink (or at least promote and/or facilitate crosslinkage of) the ECM material sheet to an amine-containing object, e.g., another isolated, sheet-form ECM material, to bond (or at least help bond) the ECM material sheet to the other object. In this context, a multilaminate ECM construct can be formed in accordance with the present invention by causing or allowing imine bonds to form between surface regions of two or more layers of ECM material. Illustratively, formation of a multilayer device can include stacking two or more ECM segments (e.g., strips of submucosa) after treating surface regions of one or both segments with a periodate. In one aspect, formation of a two-layer product includes overlapping at least a portion of one strip of submucosal tissue with at least a portion of another strip of submucosal tissue, and then fusing the strips together in the presence of sodium periodate to form a sheet of tissue material having a surface area larger than any one of the component strips of submucosal tissue. In other forms, formation of a multilaminate ECM material can include periodate treating all or a portion of one ECM segment, and then folding the segment over itself at least one time. FIG. 1 depicts a multilayered medical product 20 including two layers of porcine SIS bonded together in accordance with the present invention. As discussed more thoroughly below, this and other sheet-form graft products of the invention find wide use in the field of medicine. Illustratively, such sheets can be used to form hernia repair patches and other sheet or sheet-like products, or alternatively, can be further processed into other shapes and configurations to provide various grafting products and medical devices (e.g., occlusive and other plug devices, tissue bulking devices, tissue enhancement and other cosmetic devices, urethral slings, wound care patches and other wound care products, prosthetic valves including vascular valves, prosthetic valve leaflets and other valve components including vascular valve leaflets, etc.).

Although the multilaminate construct of FIG. 1 is formed with two layers of ECM material, multilaminate constructs of the invention can include any suitable number of layers of ECM material bonded to one another, for example, three, four, five, six, seven, eight, or more layers of ECM material bonded to one another. Further, although not necessary to broader aspects of the invention, in some embodiments, non-native Schiff's base crosslinks formed within and/or between layers of a multilaminate ECM construct to wholly or partially bond the layers together are supplemented with one or more other fusing or bonding techniques such as but not limited to chemical crosslinking, vacuum pressing under dehydrating conditions, and/or the use of adhesives, glues, and other bonding agents. Illustratively, a suitable bonding technique can include compressing ECM material layers together under dehydrating conditions in the presence of periodic acid or a salt thereof. In some forms, an already formed multilaminate product, regardless of how it was formed, is modified through suitable contact with a periodate. In other forms, ECM material layers are individually modified in accordance with the present invention and then combined to form a multilaminate product, for example, using any of the bonding techniques described herein.

Suitable bonding agents may include, for example, collagen gels or pastes, gelatin, or other agents including reactive monomers or polymers, for example cyanoacrylate adhesives. As well, bonding can be achieved or facilitated between ECM material layers using chemical crosslinking agents known in the art. Crosslinking of ECM materials can also be catalyzed by exposing the matrix to UV radiation, by treating the collagen-based matrix with enzymes such as transglutaminase and lysyl oxidase, and by photocross-linking. Nonetheless, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. In some forms, these and other suitable crosslinking techniques are used to enhance one or more physical, chemical, biological and/or other characteristics of a single-sheet or non-sheet-form ECM material before and/or after it is modified in accordance with the present invention.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization, e.g., subjecting the materials to freeze-drying or evaporative cooling conditions. Lyophilization is also useful in drying operations involving graft products of the present invention. For example, a medical product including ECM material may be subjected to lyophilization conditions before placing it in packaging for transport or storage.

Another method of dehydration bonding comprises pulling a vacuum on the assembly while simultaneously pressing the assembly together. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With suitable compression and dehydration, the ECM materials can be caused to form a generally unitary ECM structure.

During any bonding operation that involves compressing two or more material layers together to form a multilaminate construct (e.g., a vacuum pressing operation, etc.), it should be noted that the material layers can be compressed in any suitable manner including but not limited to placing the material layers, or any portions thereof, in a press, between rollers, and the like. Also, the material layers, or any portions thereof, may be compressed at any point in time during a bonding operation. Although not necessary to broader aspects of the invention, in certain forms, a multilaminate construct comprises a plurality of similarly-sized sheets of remodelable ECM material bonded together, wherein the sheets substantially overlap one another. In such aspects, at least one region of the multilaminate construct can be compressed differently than at least one other region of the construct. Illustratively, a peripheral region of the construct can be compressed with a certain amount of pressure, while an inner region of the construct can be compressed with relatively less pressure (or no pressure), or vice versa. Alternatively, certain regions of the construct can be compressed so as to form a particular pattern, e.g., repeating geometrical shapes of the same size or different sizes, across the top and/or bottom surface of the construct, or any portions thereof, wherein other regions of the construct are compressed with relatively less pressure or no pressure at all.

Again, suitable ECM starting materials can include flowable or otherwise conformable collagenous ECM materials that are at least partially solubilized or otherwise denatured or disassembled relative to their native collagenous structures. Illustratively, a suitable conformable ECM starting material may comprise an ECM material paste, a fluidized ECM material, and/or gelatinous ECM material. In some forms, the ECM starting material comprises a flowable composition comprising solubilized or suspended ECM material such as an ECM hydrolysate material.

A flowable or otherwise conformable ECM starting material can be modified as described herein to selectively enhance one or more physical, chemical, biological and/or other properties of the material such as but not limited to its anti-immunogenicity and/or biostability. In certain aspects, a gel or other conformable ECM material is treated with periodic acid or a salt thereof for a period of time and under conditions effective to increase the coherency of the ECM material or at least promote and/or facilitate a subsequent increase in the coherency of the ECM material, while preserving the activity of one or more bioactive substances retained in the ECM material such as but not limited to one or more growth factors.

Suitable flowable, remodelable ECM materials for use in this aspect of the invention can be prepared, for example, as described in U.S. Pat. Nos. 5,275,826, 5,516,533, 6,206,931, and/or 6,444,229 or in International Publication No. WO2005020847 (Cook Biotech Incorporated) published Mar. 10, 2005, which are each hereby incorporated by reference in their entirety. Such flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the flowable ECM components, with preferred ECM particulate to ECM flowable component weight ratios (based on dry solids) being about 0.1:1 to about 200:1, more preferably in the range of 1:1 to about 100:1. The inclusion of such ECM particulates in the ultimate graft product can serve to provide additional material that can function to provide bioactivity to the product (e.g. itself including FGF-2 and/or other growth factors or bioactive substances as discussed herein) and/or serve as scaffolding material for tissue ingrowth. In certain embodiments, such ECM particulates include modified ECM particulates of the present invention.

In particular aspects, a flowable ECM composition that has been modified in accordance with the present invention will exhibit the capacity to reassemble or otherwise solidify upon adjusting the pH of a relatively more acidic liquid medium containing it to about 5 to about 9, more preferably about 6.6 to about 8.0, and typically about 7.2 to about 7.8, thus inducing fibrillogenesis and matrix assembly. In one embodiment, the pH of the flowable ECM material can be adjusted by the addition of a buffer that does not leave a toxic residue, and has a physiological ion concentration and the capacity to hold physiological pH. Examples of suitable buffers include PBS, HEPES, and DMEM. Illustratively, the pH of a fractionated ECM hydrolysate can be raised by the addition of a buffered NaOH solution to 6.6 to 8.0, more preferably 7.2 to 7.8, to facilitate the formation of a modified ECM graft product. Any suitable concentration of NaOH solution can be used for these purposes, for example, including about 0.05 M to about 0.5 M NaOH. In accordance with an embodiment, a flowable ECM material is mixed with a buffer, and sufficient 0.25 N NaOH is added to the mixture to achieve the desired pH. If desired at this point, the resultant mixture can be aliquoted into designated cultureware and incubated at 37° C. for 0.5 to 1.5 hours as part of forming a modified ECM graft product.

Flowable or otherwise conformable ECM materials useful in some forms of the invention can be prepared to have desirable properties for handling and use. For example, a fluidized ECM hydrolysate can be prepared in an aqueous medium, which can thereafter be caused or allowed to form a gel for use in the invention. Such prepared aqueous mediums can have any suitable level of ECM hydrolysate therein. Typically, the ECM hydrolysate will be present in the aqueous medium at a concentration of about 2 mg/ml to about 200 mg/ml, more typically about 8 mg/ml to about 120 mg/ml, and in some embodiments about 10 mg/ml to about 75 mg/ml. In certain illustrative forms, an aqueous ECM hydrolysate composition to be used to form a graft product of the invention will have an injectable character, for example, by injection through a needle having a size in the range of 18 to 31 gauge (internal diameters of about 0.047 inches to about 0.004 inches). Further, flowable ECM compositions can be prepared so that in addition to neutralization, heating to physiologic temperatures (such as 37° C.) will substantially reduce the assembly time of the material.

It should be noted that the ionic strength of a solubilized or otherwise conformable ECM material is believed to be important in maintaining the fibers of collagen in a state that allows for fibrillogenesis and matrix assembly upon neutralization of the solubilized ECM in certain forms of the invention, and accordingly, if needed, the salt concentration of the flowable ECM material can be reduced prior to a reconstitution or other reassembly step. This holds true for any reconstitution or reassembly step including but not limited to ones to form castings, particulate products, and device coatings in accordance with the present invention. Also, the flowable ECM material can be reconstituted or otherwise reassembled at any suitable temperature, e.g., ranging from about 4° C. to about 40° C. The temperature will typically affect the reconstitution times, which may, in certain embodiments, range from about 5 to about 120 minutes at the higher reassembly temperatures and about 1 to about 8 hours at the lower reassembly temperatures.

In certain embodiments, a conformable ECM starting material is subjected to controlled oxidation conditions (e.g., through contact with sodium periodate) so that little or no bonding occurs between (i) reactive aldehyde groups formed on components of the ECM material during an oxidation step; and (ii) amine groups present in or otherwise associated with the ECM material. When formed, such oxidized materials can be subjected to further processing at that time, or alternatively, can be packaged or otherwise stored for later processing, shipment, etc.

ECM materials that have been oxidized in accordance with the present invention can be manipulated at a later point in time to cause or allow intermolecular and/or intramolecular Schiff's base crosslinks to form between at least some of the aldehyde groups present therein and amine groups present in the ECM material and/or in another object or material. For example, components of a conformable ECM material having reactive aldehyde groups formed thereon in accordance with the present invention can be later subjected to conditions suitable to cause or allow the ECM material to reconstitute or otherwise reassemble, for example, as described below. However, it is to be understood that in certain aspects, non-native Schiff's base crosslinks are formed in an ECM material nearly simultaneously with, i.e., a fraction of a second after, the production of reactive aldehyde groups in accordance with the invention.

In certain preferred aspects of the invention, a suitable flowable or otherwise conformable ECM material that has been modified in accordance with the present invention to form reactive aldehyde groups on certain components of the ECM material is thereafter caused or allowed to reconstitute or otherwise reassemble, whereby intermolecular and/or intramolecular Schiff's base crosslinks are formed between certain components of the ECM material and one or more bioactive substances are entrained in the ECM material. The degree or extent of reassembly caused or allowed in any particular embodiment can vary. In some embodiments, less than full reassembly is carried out, and a flowable product is formed that includes modified ECM material in particulate form. Such a product can then be subjected to one or more additional processing steps, for example, a reduction step using a mild reducing agent and/or a drying step as described above.

In other embodiments, full or substantially full reassembly of a conformable ECM material is carried out. Illustratively, a reconstitution step of the invention can be used to manufacture a formed, coherent, porous body comprising particulate remodelable ECM material. In some forms, such a step involves placing the ECM material that is to be reconstituted in a suitable mold, form, or other similar device (and optionally inhibiting any exposure of the material to air drying). When formed, such a formed, coherent, porous body may be further modified or otherwise manipulated as described elsewhere herein, for example, by any suitable physical, chemical, and/or biological modification step (e.g., subjected to drying conditions so as to form a dried, porous body and optionally ground to form a powdered ECM product). In certain modes of operation, such inventive ECM products are prepared so as to be insoluble or substantially insoluble in physiologic fluids at physiologic temperatures.

A reconstitution step of the invention can be carried out in any suitable manner. In an illustrative embodiment, a formed, coherent, porous body is formed by first mixing a flowable, acidic remodelable SIS material with a suitable oxidizing agent (e.g., with 0.01 M $NaIO_4$), and allowing the composition to sit for a suitable period of time. The oxidized SIS material is then poured into a mold (with the mold covered to inhibit air drying of the material) and allowed to sit for a suitable period of time to form a reconstituted or otherwise reassembled product. In some forms, this reconstituted product (while in the mold) is then lyophilized to form a dried, porous body.

In other forms, a reconstitution step in accordance with the invention comprises subjecting the ECM material to drying conditions effective to induce, promote, and/or facilitate self-assembly of collagen fibers contained in the material and entrain at least one bioactive agent in the ECM material. Suitable drying methods can include but are not limited to air drying and lyophilization techniques such as those previously described. In these forms, the drying time can vary from a few seconds to several days. A suitable drying time can depend on a number of factors including but not limited to one or more properties of the conformable ECM material and/or the drying technique used, as well as the extent or degree of collagen self-assembly desired. In this regard, different combinations of such factors can be developed through routine experimentation so as to provide a reconstituted ECM product having suitable characteristics for a particular application. For example, reconstitution times can be varied by adjusting the temperature of the air in an air drying process. It should be noted that solubilized ECM material will typically be effective to self-assemble at elevated temperatures, for example, at about 37° C. Accordingly, in certain embodiments, reconstituted ECM products of the present invention are formed by subjecting conformable ECM materials to such elevated temperatures, and in some forms, placing the conformable ECM materials in an incubator. Again, it is advantageous in some aspects of the invention to perform drying operations under relatively mild temperature exposure conditions that minimize deleterious effects upon the modified ECM materials of the invention, for example, native collagen structures and potentially bioactive substances present.

In addition or as an alternative to such reassembly techniques, a reconstitution step of the invention may involve adding to a conformable ECM starting material (or otherwise suitably contacting a conformable ECM starting material with) a suitable liquid medium for a period of time and under conditions effective to induce, promote, and/or facilitate self-assembly of collagen fibers contained in the material and entrain at least one bioactive agent in the ECM material. Further, this contact time can be varied to manipulate one or more characteristics of the reconstituted ECM product formed, for example, the product's density, porosity, and/or compressibility. In some embodiments, the network thus formed is generally homogeneous.

In certain embodiments, such a liquid medium is effective to induce fibrillogenesis and thereafter facilitate and/or promote self-assembly of the collagen fibers without having to add other materials to and/or otherwise manipulate the system, for example, without having to alter the temperature and/or pH of the system. (In this context, the term "system" refers to at least the combination of a treated conformable ECM material and a liquid medium.) In these embodiments, the contact time between the conformable ECM material and the liquid medium can be from a fraction of a second to several days. A suitable contact time to form a reconstituted ECM product in accordance with the present invention can depend on a number of factors including but not limited to one or more properties of the treated conformable ECM material and/or the liquid medium used, as well as the extent or degree of collagen self-assembly desired. In this regard, different combinations of such factors can be developed through routine experimentation so as to provide a coated embolization device having suitable characteristics for a particular application.

In some forms, an amount of solubilized SIS is introduced into a buffered aqueous medium to provide a formed, coherent, porous body comprising particulate remodelable SIS material. Any suitable buffered aqueous medium may be utilized in this regard, and advantageously, a buffered aqueous medium will be selected so as not to leave a toxic residue on or within the product formed, and to have a physiological ion concentration and the capacity to hold physiological pH. Suitable buffered aqueous mediums for such purposes may include any of the buffers previously disclosed for preparing a suitable starting ECM gel material, e.g., PBS, HEPES, or DMEM. In some forms, an ECM gel is introduced into a buffer bath to form a porous ECM product. In this regard, portions of the ECM gel may have already undergone a certain amount of fibrillogenesis. Accordingly, introducing such a gel material into a buffer bath or other suitable liquid medium will further the fibrillogenesis and matrix assembly, leading to a reconstituted ECM product in accordance with the present invention.

In one aspect of the invention, a formed, coherent, porous body is formed by first mixing a flowable, acidic remodelable SIS material with a suitable oxidizing agent (e.g., with 0.01 M $NaIO_4$), and allowing the composition to sit for a suitable period of time. The oxidized SIS material can then be mixed with a suitable neutralizing agent (e.g., with 0.25 M NaOH). This mixture can then be poured into a mold (with the mold optionally covered to inhibit air drying of the material) and allowed to sit for a suitable period of time to form a reconstituted or otherwise reassembled product. In some forms, this reconstituted product (while in the mold) is then lyophilized to form a dried, porous body.

In certain embodiments, a liquid medium (at least as initially provided) is not configured to induce self-assembly of collagen fibers contained in a conformable ECM material (or at least not to the extent of the liquid mediums described above). In such embodiments, self-assembly of these collagen fibers is induced and carried out by further manipulating the system, for example, by adding other materials to the system and/or altering certain properties of the system such as but not limited to its temperature, pH, and/or the like. For example, it should be noted that solubilized ECM material will typically be effective to self-assemble at elevated temperatures, for example, at about 37° C. Accordingly, in certain embodiments, a reconstituted ECM material product in accordance with the present invention can be formed by placing a solubilized ECM material in a liquid medium, and thereafter suitably raising the temperature of the system to allow or cause collagen fibers contained therein to self-assemble. In this regard, reconstitution times can be varied by adjusting the temperature of the liquid medium utilized. In certain aspects, solubilized ECM materials are reconstituted under gravitational force of less than one gravity, preferably about zero gravity.

Graft materials of the invention find wide application in the field of medicine, and in this regard, can be adapted to provide any device or object that is suitable for application to and/or implantation within a patient. The invention further provides methods of treatment that utilize such graft materials, for example, methods to replace, augment, repair, and/or otherwise suitably treat diseased or otherwise damaged or defective tissue of a patient. Illustratively, a medical patch or similar graft product comprising a medical material of the invention can be used as a tissue support device such as in a hernia repair procedure. In some embodiments, graft materials of the invention are configured as implantable devices suitable for bulking tissue, providing hemostasis, and/or providing occlusion in a passageway or other open space within the body of a patient.

In certain aspects, single- and multilayered graft materials provide wound healing products suitable for cutaneous, intracutaneous, and/or subcutaneous wound treatment, e.g., a hernia repair patch or a burn treatment material. In some forms, multilaminate medical materials of the invention will be constructed so as to provide an overall device thickness of at least about 150 microns, typically ranging from about 150 to about 1000 microns, and in certain embodiments ranging from about 200 to about 1000 microns. Such relatively thick layers can provide advantageous and lasting ECM material scaffolds for tissue ingrowth, especially in the field of wound care such as burn and ulcer care. In addition to such thicknesses, typical graft products of the invention in sheet-form will have lengths and widths ranging from about 2 cm to about 50 cm.

In certain embodiments, it may be advantageous to process a medical graft material of the invention, or any portion thereof, so that it exhibits a meshed structure. Illustratively, a meshed structure can have a plurality of slits therein to provide a mesh pattern, and the mesh pattern can be useful to provide deformability to the structure, and in some case, expandability. In this regard, in some meshed constructs, expansion or other deformation of the structure will widen the openings created by the slits of the mesh pattern, by lateral and/or vertical displacement of the edges of the slits relative to one another. Certain meshed devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the graft product, particularly in the field of wound care.

A meshed pattern can be created using suitable meshing devices designed for processing skin autograft sections. Such devices can include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-throughput method of preparing meshed material layers or graft devices of the invention. It will be understood, however, that the mesh pattern can be made by hand-cutting the material or by using appropriate cutting tools with multiple blades to cut the slits to provide the mesh pattern.

Alternatively, graft products of the invention may find use as precursor materials for forming a variety of other medical devices, or components thereof. Illustratively, graft materials of the invention can be processed into various shapes and configurations, for example, into a urethral sling or a prosthetic body part. In some forms, sheet-form graft materials of the invention are suitable for forming tubular grafting devices, which may be used to replace a circulation vessel, or a portion thereof, or to bypass a blocked vessel.

In some aspects of the invention, graft materials are used as exterior, interior, and/or other coverings for supporting frames including but not limited to those used to provide stents and valve structures (e.g., prosthetic heart valves and other flow-modifying devices useful in the vascular system or in other bodily systems involving the flow of bodily substances through a passageway or opening). These applications include, for example, those utilizing self-expanding or otherwise expandable frames. In one mode of forming a valve structure, an inventive graft material can be attached to a frame in a fashion whereby it forms one, two, or more leaflets, cusps, pockets or similar structures that resist flow in one direction relative to another. In a specific application, such devices are constructed as implantable vascular valves to treat venous insufficiencies in humans, for example, occurring in the legs. In other applications, valves for treating these or other valve deficiencies may be constructed without the use of a frame or other supporting structure. For example, an inventive graft material can be adapted to provide a monocusp valve in a vascular vessel, or, alternatively, it can be adapted to provide a multicuspid valve in a vascular vessel, wherein the multicuspid valve comprises a plurality of cusps. In this respect, such materials can be adapted to provide a bicuspid valve, a tricuspid valve, or a quadracuspid valve in a vascular vessel, wherein any of these valves may or may not be attached to or otherwise associated with one or more frame elements. Illustratively, an inventive valve structure can incorporate a suitable ECM material (e.g., porcine SIS) that has been soaked in or otherwise treated with sodium periodate at a suitable concentration (e.g., 0.001 M to 0.1 M) and for a suitable amount of time (e.g., about 15 minutes to about 3 days) to achieve a desired ECM material modification. Such modification of an ECM material can occur before or after the ECM material is used in forming a valve structure.

Some embodiments of the invention provide medical products which are comprised of medical graft materials such as any of those described herein enclosed within sterile medical packaging. Illustratively, such a medical product can have packaging including a backing layer and a front film layer that are joined by a boundary of pressure-adhesive as is appropriate for medical packaging, wherein the contents of the packaging are sealed between the backing layer and front film layer.

Sterilization of such a medical product may be achieved, for example, by irradiation, ethylene oxide gas, or any other suitable sterilization technique, and the materials and other properties of the medical packaging will be selected accordingly. Also, medical graft materials of the invention can be contained in a sterile packaging in any suitable state. Suitable states include, for example, a hydrated or dehydrated state. The devices can be dehydrated by any means known in the art (e.g., lyophilization or air dried). If medical graft materials of the present invention are stored in a dehydrated state, it is preferred that they retain all of its biological and mechanical properties (e.g., shape, density, flexibility, etc.) upon rehydration.

Additionally, the package can include indicia to communicate the contents of the package to a person, machine, computer, and/or electronic device. Such indicia may include the dimensions of, the type of materials used to form, and/or the physical state of, the contents of the package. In certain embodiments, the medical graft materials are packaged for sale with instructions for use. For example, in certain embodiments, a medical product includes at least one device comprising an inventive medical graft material sealed within a sterile package, wherein the packaging has visible indicia identifying the at least one device as being suitable for a particular application, and/or contains or is otherwise associated with printed materials that identify, and potentially describe the use of, the contents of the package. The packaging could also include visible indicia relating to the dimension of the at least one device, and/or relating to treatment site(s) for which the at least one device is suited.

As used in the specification and claims, the terms "a" and "an," when used in conjunction with the terms "comprising", "including" and "having" and related words, are intended to mean one or more.

In order to promote a further understanding of the present invention and its features and advantages, the following specific examples are provided. However, it will be understood that these examples are illustrative and are not limiting of the invention.

EXAMPLE 1

First, a "high density" SIS digest material was formed. A powdered (produced by cryogrinding isolated/washed but non-disinfected) porcine small intestinal submucosa was frozen in a −80° C. freezer. Then, the frozen SIS powder was removed from the freezer and centrifuged at 7000 rpm for 30 minutes to obtain an SIS paste. This SIS paste was placed in a container with a solution of HCl (50 grams of SIS per L of HP water used; 10 mL of 1N HCl per L of HP water used). Pepsin was then added to the container (1 gram of pepsin per L of HP water used), and the paste was allowed to digest for 48-72 hours with constant stirring. This digest was then centrifuged at 15,000 rpm for 45 minutes at 4° C. After removing the supernatant, the solids of the digest were lyophilized. 100 mg of this lyophilate was then added to 1.5 mL of 0.01 M HCl, and placed in a dialysis tube (3500 MW cut off). The filled tube was placed in cylindrical jar containing 0.2% PAA (peracetic acid) for 2 hours. The PAA-treated digest was then dialysed against 0.01 M HCl for at least 48 hours to obtain the high density SIS digest material. This high concentration SIS digest was then mixed with 0.01 M NaIO4 (final solution concentration) and allowed to sit for 2 hours. The NaIO4-treated digest was neutralized with 10×PBS & 0.25 M NaOH solutions to obtain a final pH of 7-8.5. The neutralized intermediate product was mixed for a short period of time and poured into a mold (with the mold covered to inhibit air drying of the intermediate product) and allowed to sit for 30 minutes to 1 hour to obtain a reconstituted or otherwise reassembled product. The reconstituted product notably released an amount of water during the reconstitution process. Then, the reconstituted product (while in the mold) was placed in a −80° C. (F?) freezer and lyophilized to form a dried, porous body. Upon rehydration, the formed, coherent, porous body generally maintained its original shape.

EXAMPLE 2

First, a "high density" SIS digest material was formed. A powdered (produced by cryogrinding isolated/washed but non-disinfected) porcine small intestinal submucosa was frozen in a −80° C. freezer. Then, the frozen SIS powder was removed from the freezer and centrifuged at 7000 rpm for 30 minutes to obtain an SIS paste. This SIS paste was placed in a container with a solution of HCl (50-60 grams of SIS per L of HP water used; 10 mL of 1N HCl per L (kg?) of HP water used). Pepsin was then added to the container (1 gram of pepsin per L of HP water used), and the paste was allowed to digest for 48-72 hours with constant stirring. This digest was then centrifuged at 15,000 rpm for 45 minutes at 4° C. After removing the supernatant, the solids of the digest were lyophilized. 100 mg of this lyophilate was then added to 1.5 mL of 0.01 M HCl, and placed in a dialysis tube (3500 MW cut off). The filled tube (?) was placed in cylindrical jar containing 0.2% PAA (peracetic acid) for 2 hours. The PAA-treated digest was then dialysed against 0.01 M HCl for at least 48 hours to obtain the high concentration SIS digest material. This high concentration SIS digest was then mixed with 0.01 M sodium periodate in lot # P104391, and allowed to sit for 2 hours at room temperature. The periodate-treated SIS was placed in a refrigerator at 1-4° C. for 2-7 days, and in some case for 5-7 days. The formed, coherent, porous body was acidic (pH<6.0), and was found to be stable after 2 days in pH 7.4 water.

EXAMPLE 3

In this example, particulate SIS with enhanced biodegradation resistance was formed. First, virally deactivated SIS sheets (400 grams) were mixed with 1500 HP water and 207 mL 0.1 M NaIO4, and allowed to sit for 2 hours. The periodate-treated SIS sheets were rinsed for 2 hours, subjected to a triple wash in HP water, dried (e.g., air dried or lyophilized), and cryoground. The ground SIS was then sieved to obtain particulates of particular sizes, shapes, etc., and sterilized (e.g., with EtO or e-beam).

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical graft material, comprising:
a layer of isolated remodelable extracellular matrix material that has been modified through contact with periodic acid or a salt thereof to introduce non-native Schiff base crosslinks between components of the extracellular matrix material and enhance the biostability of the extracellular matrix material; and
at least one bioactive agent native to an animal source tissue for the extracellular matrix material retained in the modified extracellular matrix material layer, the bioactive agent selected from the group consisting of a proteoglycan, a growth factor, a glycoprotein, and a glycosaminoglycan.

2. The medical graft material of claim 1, wherein said modified extracellular matrix material layer comprises submucosa.

3. The medical graft material of claim 2, wherein said submucosa comprises porcine submucosa.

4. The medical graft material of claim 2, wherein said submucosa comprises small intestine submucosa, urinary bladder submucosa, or stomach submucosa.

5. The medical graft material of claim 1, wherein said modified extracellular matrix material layer comprises serosa, pericardium, dura mater, peritoneum, or dermal collagen.

6. The medical graft material of claim 1, comprised of a multilaminate construct in which said modified extracellular matrix material layer provides a first layer, said multilaminate construct also including at least a second isolated remodelable extracellular matrix material layer bonded to said first layer at least in part through said non-native Schiff base crosslinks.

7. The medical graft material of claim 1, further comprising at least one additional bioactive agent added to the modified extracellular matrix material layer.

8. The medical graft material of claim 7, wherein said at least one additional bioactive agent is non-native to the source of the extracellular matrix material layer.

9. The medical graft material of claim 7, wherein a Schiff's base crosslink bonds said at least one additional bioactive agent to said modified extracellular matrix material.

10. The medical graft material of claim 1, wherein said modified extracellular matrix material layer is a first material layer, and wherein said medical graft material further includes a second layer of isolated remodelable extracellular matrix material coupled or bonded to said first material layer.

11. The medical graft material of claim 10, wherein said second extracellular matrix material layer has been modified through contact with periodic acid or a salt thereof.

12. The medical graft material of claim 10, further comprising one to eight additional layers of extracellular matrix material, wherein said one to eight additional extracellular matrix material layers have been modified through contact with periodic acid or a salt thereof.

13. A medical graft material, comprising:
a layer of isolated remodelable extracellular matrix material that has been modified to introduce non-native Schiff base crosslinks between components of the extracellular matrix material and enhance the biostability of the extracellular matrix material; and at least one bioactive agent native to an animal source tissue for the extracellular matrix material retained in the modified extracellular matrix material layer, the bioactive agent selected from the group consisting of a proteoglycan, a growth factor, a glycoprotein, and a glycosaminoglycan.

14. The medical graft material of claim 13, wherein the extracellular matrix material has been treated with a reducing agent and an amine-containing compound after modification to introduce said non-native Schiff base crosslinks.

15. The medical graft material of claim 13, wherein the extracellular matrix material comprises submucosa, renal capsule membrane, dermal collagen, dura mater, pericardium, fascia lata, serosa, peritoneum or basement membrane.

16. The medical graft material of claim 13, comprised of a multilaminate construct in which said modified extracellular matrix material layer provides a first layer, said multilaminate construct also including at least a second isolated remodelable extracellular matrix material layer bonded to said first layer at least in part through said non-native Schiff base crosslinks.

17. The medical graft material of claim 13, wherein said layer of isolated remodelable extracellular matrix material that has been modified by contact with a periodate to introduce said non-native Schiff base crosslinks.

18. The medical graft material of claim 17, wherein the extracellular matrix has been modified to introduce non-native Schiff base crosslinks between components of the extracellular matrix material and enhance the biostability of the extracellular matrix material.

19. The medical graft material of claim 17, wherein the extracellular matrix has been modified to introduce non-native Schiff base crosslinks between components of the extracellular matrix material and enhance the anti-immunogenicity of the extracellular matrix material.

20. A medical graft material, comprising:

a layer of isolated extracellular matrix material that retains at least one of a proteoglycan, a growth factor, a glycoprotein, and a glycosaminoglycan, from an animal source tissue for the layer of isolated extracellular matrix material; and wherein said extracellular matrix material has been modified through contact with periodic acid or a salt thereof so as to enhance the biostability of the extracellular matrix material.

21. The medical graft material of claim 20, wherein the extracellular matrix material has been treated with an amine-containing compound after the modification through contact with the periodic acid or salt thereof.

22. The medical graft material of claim 20, wherein the extracellular matrix material has been modified through contact with sodium periodate.

23. The medical graft material of claim 20, wherein the extracellular matrix material comprises submucosa, renal capsule membrane, dermal collagen, dura mater, pericardium, fascia lata, serosa, peritoneum or basement membrane.

* * * * *